United States Patent [19]

Bindra

[11] 4,091,207

[45] May 23, 1978

[54] PROSTAGLANDIN INTERMEDIATE INCLUDING OXATHIO HETEROCYCLIC RING

[75] Inventor: Jasjit Singh Bindra, Groton, Conn.

[73] Assignee: Pfizer Inc., New York, N.Y.

[21] Appl. No.: 774,904

[22] Filed: Mar. 7, 1977

Related U.S. Application Data

[62] Division of Ser. No. 679,345, Apr. 22, 1976, abandoned.

[51] Int. Cl.$^2$ .................. C07C 117/00; C07D 327/04; C07D 327/06; C07D 411/04
[52] U.S. Cl. .............................. 542/429; 260/327 M; 260/327 P; 542/430
[58] Field of Search .......... 260/308 D, 240 R, 327 M, 260/327 P; 542/429, 430

[56] References Cited

U.S. PATENT DOCUMENTS

| | | | |
|---|---|---|---|
| 3,794,669 | 2/1974 | Wynberg et al. | 260/397.2 |
| 3,883,513 | 5/1975 | Hess et al. | 260/240 R |
| 3,935,240 | 1/1976 | Mallion | 260/240 R X |
| 3,947,469 | 3/1976 | Ghosez et al. | 260/327 M |
| 3,954,741 | 5/1976 | Schaaf et al. | 260/240 R |
| 4,024,181 | 5/1977 | Babej et al. | 260/240 R X |

OTHER PUBLICATIONS

Jour. Am. Chem. Soc. 75, 3704 (1953) Djerassi et al.

*Primary Examiner*—Allen B. Curtis
*Attorney, Agent, or Firm*—Connolly and Hutz

[57] ABSTRACT

A novel process and intermediates for the synthesis of prostaglandin and their analogs are disclosed.

10 Claims, No Drawings

PROSTAGLANDIN INTERMEDIATE INCLUDING OXATHIO HETEROCYCLIC RING

CROSS REFERENCE TO RELATED APPLICATION

This application is a division of application Ser. No. 679,345 filed Apr. 22, 1976 and now abandoned.

BACKGROUND OF THE INVENTION

This invention relates to a novel process for the synthesis of prostaglandins and their analogs and synthetic intermediates employed in this process.

The prostaglandins are C-20 unsaturated fatty acids which exhibit diverse physiological effects. Each of the known naturally occurring prostaglandins is derived from prostanoic acid which has the structure and position numbering:

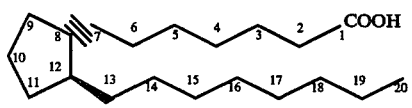

[Bergstrom et al., Pharmacol. Rev. 20, 1 (1968), and references cited therein.] A systematic name for prostanoic acid is 7-[(2β-octyl)-cyclopent-1α-yl]heptanoic acid.

PGA$_2$ has the structure:

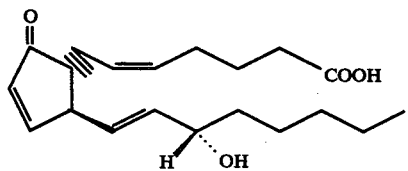

PGB$_2$ has the structure:

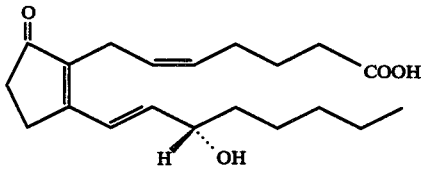

PGE$_2$ has the structure:

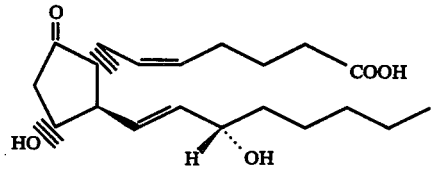

PGF$_{2\alpha}$ has the structure:

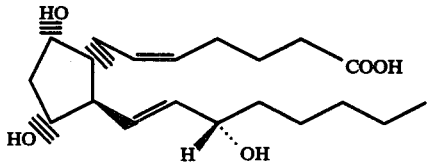

PGF$_{2\beta}$ has the structure:

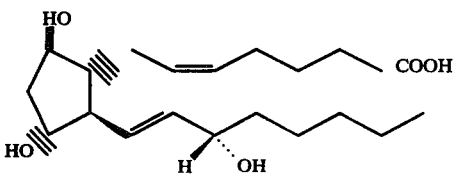

Each of the PG$_1$ prostaglandins, PGE$_1$, PGF$_{1\alpha}$, PGF$_{1\beta}$, PGA$_1$, and PGB$_1$, has a structure the same as the corresponding PG$_2$ compound except that the cis double bond between C-5 and C-6 is replaced by a single bond. For example, PGA$_1$ has the structure:

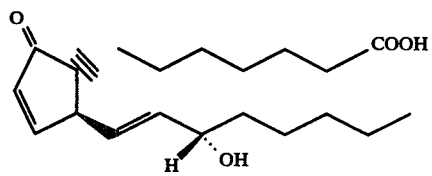

The PG$_0$ compounds are those in which there are no double bonds in either side chain. For instance, PGE$_0$ has the structure

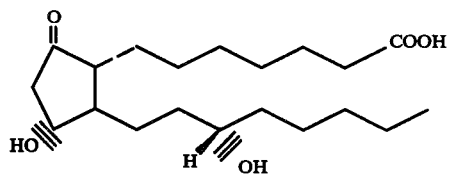

Broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in the above formulas is in S configuration. [See, Nature, 212, 38 (1966) for discussion of the stereochemistry of the prostaglandins.]

Molecules of the known prostaglandins each have several centers of asymmetry, and can exist in racemic (optically inactive) form and in either of the two enantiomeric (optically active) forms, i.e. the dextrorotatory and levorotatory forms. As drawn above, each structure represents the particular optically active form of the prostaglandin which is obtained from certain mammalian tissues, for example, sheep vesicular glands, swine lung, or human seminal plasma, or by carbonyl and/or double bond reduction of that prostaglandin. [Bergstrom et al., cited above.] The mirror image or optical antipode of each of the above structures represents the other enantiomer of that prostaglandin. For instance, the optical antipode of PGF$_{2\alpha}$ (ent-PGF$_{2\alpha}$) is drawn as

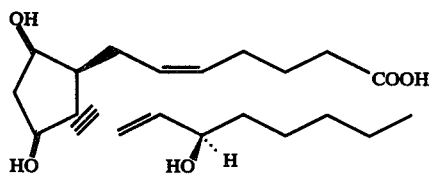

The racemic form of a prostaglandin contains equal numbers of a particular stereoisomer and its mirror image. When reference to a prostaglandin racemate is intended, the symbols "rac" or "dl" will precede the prostaglandin name. Two structures are needed to represent a racemate. For instance, the structure of dl-PGF$_{2\alpha}$ is properly represented as an equimolar mixture of PGF$_{2\alpha}$ and ent-PGF$_{2\alpha}$. The terms PGE$_1$, PGE$_2$, PGF$_{1\alpha}$ and the like as used herein will mean that stereoisomer with the same absolute configuration as the corresponding prostaglandin found in mammalian tissue.

In an optical antipode, the absolute configuration at all of the above-mentioned centers of asymmetry is inverted. In an epimer, the configuration is inverted at one or more but not all of the centers. For instance, the absolute configuration of the 15-hydroxy group in 15-epi-PGF$_{2\alpha}$ is the R configuration and is shown as

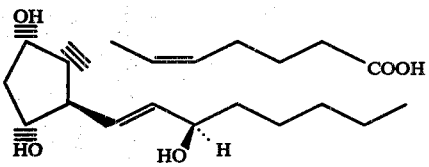

It will be noted that only the configuration at the 15-position is inverted and that at the other centers of asymmetry, namely the 8-, 9-, 11- and 12-positions, the absolute configuration is the same as that in the naturally-occurring mammalian PGF$_{2\alpha}$. Racemic mixtures of epimers may also exist for instance, if 15-keto-PGF$_{2\alpha}$ is reduced with zinc borohydride or a hindered alkyl borohydride, the resulting product is a racemic mixture of 15$\alpha$-hydroxy and 15$\beta$-hydroxy-PGF$_{2\alpha}$.

PGE$_1$, PGE$_2$, and the corresponding PGF$_\alpha$, PGF$_\beta$, PGA, and PGB compounds, and many of their derivatives such as the esters, acylates, and pharmacologically acceptable salts, are extremely potent inducers of various biological responses. These compounds are, therefore, potentially useful for pharmacological purposes. [Bergstrom et al, cited above.] A few of those biological responses are systemic arterial blood pressure lowering in the case of the PGE, PGF$_\beta$ and PGA compounds as shown in cardiac cannulated rats or dogs; pressor activity for the PGF$_\alpha$ compounds; stimulation of smooth muscle as shown by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury; and in the case of the PGE and PGB compounds, stimulation of epidermal proliferation and keratinization as shown when applied in culture to embryonic chick and rat skin segments.

Prostaglandins are useful to prevent, control, or alleviate a wide variety of diseases and undesirable physiological conditions in avians and mammals, including humans, useful domestic animals, pets, and zoological specimens, and in laboratory animals, for example, mice, rats, rabbits, and monkeys.

For example, these compounds, especially those of the E series, are useful in mammals, including man, as bronchodilators [Cuthbert, Brit. Med. J., 4: 723–726, 1969]. As nasal decongestants, the compounds are used in a dose range of about 10 μg. to about 10 mg. per ml. of a pharmacologically suitable liquid vehicle or as an aerosol spray, both for topical application.

The PGE compounds are useful in the treatment of asthma because of their activity as bronchodilators and/or as inhibitors of the release of anaphylactic, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of routes in a number of dosage forms, e.g., orally in the form of tablets, capsules, or liquids; rectally in the form of suppositories; parenterally with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day. These prostaglandins can also be combined advantageously with other anti-asthmatic agents, such as sympathomimetics (isoproterenol, phenylephrine, ephedrine, etc.); xanthine derivatives (theophylline and aminophyllin); and corticosteroids (ACTH and predinisolone). Regarding use of these compounds see South African Patent No. 68/1055.

The PGE and PGA compounds are useful in mammals, including man and animals to reduce and control excessive gastric secretion, thereby reducing or avoiding gastrointestinal ulcer formation, and accelerating the healing of such ulcers already present in the gastrointestinal tract. [Shaw and Ramwell, In: Worchester Symposium on Prostaglandins, Wiley (New York, 1968), pp. 55–64.] For this purpose, the compounds are administered parenterally by injection or intravenous infusion in an infusion dose range of about 0.1 μg. to about 500 μg. per kg. of body weight per minute, or in a total daily dose by injection or infusion in the range of about 0.1 to about 20 mg. per kg. of body weight per day.

The PGE compounds are useful whenever it is desired to inhibit platelet aggregation, to reduce the adhesive character of platelets, and to remove or prevent the formation of thrombi in mammals, including man, rabbits, and rats. [Emmons et al., Brit. Med. J., 2: 468–472, 1967.] These compounds are, for example, useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically. For rapid response, especially in emergency situation, the intravenous route of administration is preferred. Doses in the range of about 0.005 to about 20 mg. per kg. of body weight per day are used.

The PGE compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to the new body. Under such conditions, aggregated platelets tend to block the blood vessels and portions of the circulation apparatus. Such aggregation is inhibited by the presence of a prostaglandin. For this purpose, the compound is added gradually or in single or multiple portions to the circulating blood, to the blood of the donor animal, to the perfused body portion, attached to detached, to the recipient, or to two or all of those at a total steady state dose of about 0.001 to 10 mg. per liter or circulating fluid.

PGE and PGF$_\alpha$ compounds are extremely potent in causing stimulation of smooth muscle, and are also highly active in potentiating other known smooth muscle stimulators. Therefore, PGE$_2$, for example, is useful in place or or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered intravenously immediately after abortion or delivery at a dose in the range of about 0.01 to about 50 µg. per kg. of body weight per minute until the desired effect is obtained. Subsequent doses are given parenterally during puerperium in the range 0.01 to 2 mg. per kg. of body weight per day.

The PGE, PGA and PGF$_\beta$ compounds are useful as hypotensive agents and vasodilators [Bergstrom et al., Acta Physiol. Scand., 64: 332–333, 1965; Life Sci., 6: 449–455, 1967] in mammals, including man. To lower systemic arterial blood pressure, the compounds are administered by intravenous infusion at the rate of about 0.01 to about 50 µg. per kg. of body weight per minute, or in single or multiple doses of about 25 to 500 µg. per kg. of body weight total per day. [Weeks and King, Federation Proc. 23: 327, 1964; Bergstrom, et al., 1965, op. cit.; Carlson, et al., Acta Med. Scand. 183: 423–430, 1968; and Carlson et al., Acta Physiol. Scand. 75: 161–169, 1969.]

The PGA and PGE compounds and derivatives and salts thereof increase the flow of blood in the mammalian kidney, thereby increasing volume and electrolyte content of the urine. For that reason the compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the compounds are useful in alleviating and correcting cases of edema resulting from massive surface burns, in the management of shock, etc. For these purposes, the compounds are preferably first administered by intravenous injection at a dose in the range 10 to 1000 µg. per kg. of body weight or by intravenous infusion at a dose in the range 0.1 to 20 µg. per kg. of body weight per minute until the desired effect is obtained. Subsequent doses are given by intravenous, intramuscular, or subcutaneous injection or infusion in the range 0.05 to 2 mg. per kg. of body weight per day.

The PGE compounds, especially PGE$_1$, are useful in the treatment of psoriasis (Ziboh, et al., Nature, 254, 351 (1975)). For this purpose, the compound is administered topically at a dose of 1–500 µg. 1 to 4 times daily until the desired effect is obtained.

The PGE, especially PGE$_2$, PGF$_\alpha$, and PGF$_\beta$ compounds are useful in the induction of labor in pregnant female animals, including man, cows, sheep, and pigs, at or near term [Karim et al., J. Obstet. Gyaec. Brit. Cwlth., 77: 200–210, 1970] or in the induction of therapeutic abortion [Bygdeman et al., Contraception, 4, 293 (1971)]. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. Alternative routes of administration are oral, extraamniotic or intraamniotic.

The PGE, PGF$_\alpha$, and PGF$_\beta$ compounds are useful for fertility control in female mammals [Karim, Contraception, 3, 173 (1971)] including humans and animals such as monkeys, rats, rabbits, dogs, cattle, and the like. By the term ovulating female mammals is meant animals which are mature enough to ovulate but not so old that regular ovulation has ceased. For that purpose, PGF$_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

Patents have been obtained for several prostaglandins of the E and F series as inducers of labor in mammals (Belgian Pat. No. 754,158 and West German Pat. No. 2,034,641), and on PGE$_1$, F$_2$ and F$_3$ for control of the reproductive cycle (South African Patent 69/6089). It has been shown that luteolysis can take place as a result of administration of PGF$_{2\alpha}$ [Labhsetwar, Nature, 230, 528 (1971)] and hence prostaglandins have utility for fertility control by a process in which smooth muscle stimulation is not necessary.

The PGE and PGF$_2$ compounds are useful as antiarrhythmic agents (Forster, et al, Prostaglandins, 3, 895 (1973)). For this purpose the compound is infused intravenously at a dose range of 0.5–500 µg/kg/minute until the desired effect is obtained.

As mentioned above, the PGE compounds are potent antagonists of epinephrine-induced mobilization of free fatty acids. For this reason, these compounds are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful in promoting healing of skin which has been damaged, for example, by burns, wounds, and abrasions, surgery, etc. These compounds are also useful in promoting adherence and growth of skin autografts, especially small, deep (Davis) grafts which are intended to cover skinless areas by subsequent outward growth rather than initially, and to retard rejection of homografts.

To promote the growth of epidermal cells, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, such as when there is substantial fluid loss as in the case of extensive burns or skin loss due to other causes, systemic administration is advantageous. Especially in topical applications, these prostaglandins may be advantageously combined with antibiotics such as gentamycin, neomycin, polymycin B. bacitracin, spectinomycin, tetracycline and oxytetracycline; with other antibacterials such as mafenide hydrochloride, sulfadiazine, furazolium chloride, and nitrofurazone; and with corticosteroids such as hydrocortisone, prednisolone, methylprednisolone, and fluprednisolone, each being used in the combination at the usual concentration suitable for its use alone.

In the preparation of synthetic pharmaceutical agents, among the principal objects is the development of analogs of naturally occurring compounds which are highly selective in their physiological activity and which have an increased duration of activity. In a series of compounds like the naturally-occurring prostaglandins which has an extremely broad activity spectrum, increasing the selectivity of a single compound usually involves the enhancement of one physiological effect and the diminution of the others. By increasing the selectivity, one would, in the case of the natural prostaglandins, except to alleviate the severe side effects, particularly the gastrointestinal one frequently observed following systemic administration of the natural prostaglandins.

SUMMARY OF THE INVENTION

The present invention comprises a first process for preparing an optically active compound of the structure

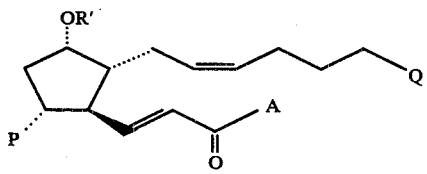

and its optical antipode and the racemic mixture thereof which comprises contacting a compound of the structure

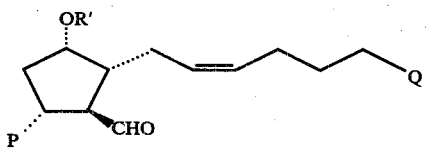

its optical antipode or the racemic mixture thereof wherein

R' is hydrogen or

and
  R" is selected from the group consisting of alkyl of from one to four carbon atoms, β-naphthyl, phenyl, p-biphenyl and phenylalkyl of from seven to nine carbon atoms;
  P is selected from the group consisting of hydrogen, tetrahydropyranyl-2-yloxy and dimethyl-t-butylsilyloxy;
  and Q is selected from the group consisting of tetrazol-5-yl,

wherein R is selected from the group consisting of hydrogen, alkyl of from one to six carbon atoms, phenyl, phenylalkyl of from seven to nine carbon atoms, β-naphthyl and p-biphenyl; R''' is alkyl of from one to four carbon atoms and phenyl with the ylide of a compound of the structure

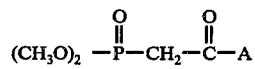

in reaction inert solvent at a temperature of from about 0° to about 80° C until the reaction is substantially complete wherein A is selected from the group consisting of alkyl of from four to eight carbon atoms, 2-indanyl, and a substituent of the structure

and
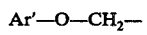

wherein n is an integer of from one to two and Ar is selected from the group consisting of α-naphthyl, β-naphthyl, α-furyl, α-thienyl, phenyl and monosubstituted phenyl and the substituent on said monosubstituted phenyl is selected from the group consisting of fluoro, chloro, trifluoromethyl, phenyl and alkyl and alkoxy of from one to six carbon atoms; and Ar' is selected from the group consisting of phenyl and monosubstituted phenyl; and the substituent on said monosubstituted phenyl is selected from the group consisting of fluoro, chloro, trifluoromethyl, phenyl, and alkyl and alkoxy of from one to six carbon atoms.

A preferred embodiment of said process is that wherein the starting material is of the structure:

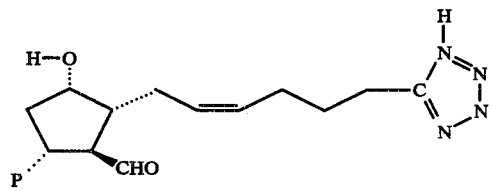

An especially preferred embodiment of said first process is that wherein the starting material is:

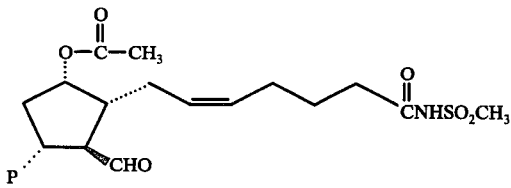

The said first process is also preferred when A is

and said first process is especially preferred when A is $C_6H_5$—$OCH_2$—.

The instant invention further comprises a second process; said process for preparing an optically active compound of the structure

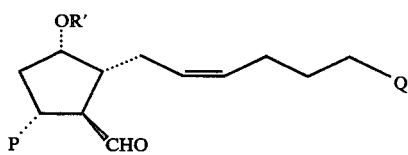

its optical antipode or the racemic mixture thereof wherein R' is selected from the group consisting of hydrogen and

and R'' is selected from the group consisting of alkyl of from one to four carbon atoms, β-naphthyl, phenyl, p-biphenyl and phenylalkyl of from seven to nine carbon atoms; Q is selected from the group consisting of tetrazol-5-yl,

wherein R is selected from the group consisting of hydrogen, alkyl of from one to six carbon atoms, phenyl, phenylalkyl of from seven to nine carbon atoms, β-naphthyl and p-biphenyl; R''' is alkyl of from one to four carbon atoms and phenyl; and P is selected from the group consisting of hydrogen, dimethyl-t-butyl-silyloxy, and tetrahydropyran-2-yloxy which comprises contacting an optically active compound of the structure

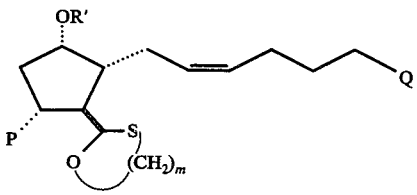

its optical antipode or the racemic mixture wherein m is two or three with mercuric chloride in reaction-inert solvent at a temperature of from about 25° to about 80° C until the reaction is substantially complete. Said second process is preferred when R' is hydrogen. Said second process wherein R' is hydrogen is further preferred when Q is COOR. Likewise said second process is preferred when R' is hydrogen and Q is tetrazol-5-yl. Said second process wherein R' is hydrogen is especially preferred when Q is $CONHSO_2 R'''$ and most especially preferred when Q is $CONHSO_2CH_3$.

Said second process is also preferred when R' is COR'' and especially when R' is $COCH_3$. Said second process wherein R' is $COCH_3$ is further preferred when Q is COOR. Said second process is likewise preferred when R' is $COCH_3$ and Q is tetrazol-5-yl. Said second process wherein R' is $COCH_3$ is especially preferred when Q is $CONHSO_2R'''$ and most especially preferred when Q is $CONHSO_2CH_3$.

The present invention further comprises a third process; said process for preparing an optically active compound of the structure

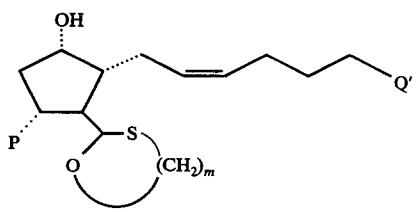

its optical antipode or the racemic mixture thereof wherein Q' is selected from the group consisting of tetrazol-5-yl,

P is selected from the group consisting of hydrogen, tetrahydropyran-2-yloxy, and dimethyl-t-butylsilyloxy; and m is two or three; which comprises contacting an optically active compound of the structure

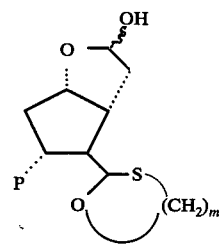

its optical antipode or the racemate thereof with a ylide of a compound of the structure

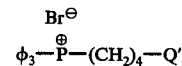

in reaction inert solvent at a temperature of from about −30° to about 80° C until the reaction is substantially complete. Said third process is preferred when Q' is COOH. Said third process is likewise preferred when Q' is tetrazol-5-yl. Said third process is especially preferred when Q' is $CONHSO_2R'''$ and most especially preferred when Q' is $CONHSO_2CH_3$.

In addition the present invention contemplates novel intermediates as follows:

An optically active compound of the structure

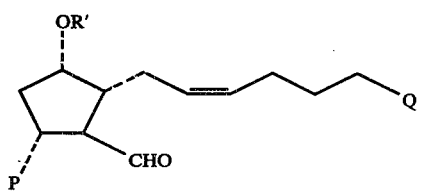

its optical antipode and the racemic mixture thereof wherein:

R' is hydrogen or

and

R" is selected from the group consisting of alkyl of from one to four carbon atoms, β-naphthyl, phenyl, p-biphenyl and phenylalkyl of from seven to nine carbon atoms;

P is selected from the group consisting of hydrogen, tetrahydropyran-2-yloxy and dimethyl-t-butylsilyloxy;

and Q is selected from the group consisting of tetrazol-5-yl,

wherein R is selected from the group consisting of hydrogen, alkyl of from one to six carbon atoms, phenyl, phenylalkyl of from seven to nine carbon atoms, β-naphthyl and p-biphenyl; and R''' is alkyl of from one to four carbon atoms or phenyl.

an optically active compound of the structure

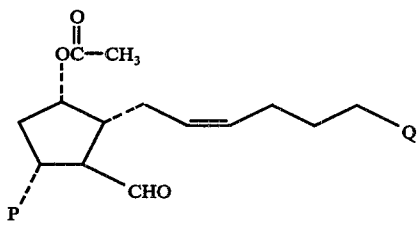

a compound of formula B its optical antipode or a racemic mixture thereof wherein Q is COOR; a compound of formula B its optical antipode or a racemic mixture thereof wherein Q is COOH; a compound of formula B its optical antipode or a racemic mixture thereof wherein Q is COOCH₃; a compound of formula B its optical antipode or a racemic mixture thereof wherein Q is CONHSO₂R'''; a compound of formula B its optical antipode or a racemic mixture thereof wherein Q is CONHSO₂CH₃; a compound of formula B its optical antipode or a racemic mixture thereof wherein Q is tetrazol-5-yl.

A compound of the formula:

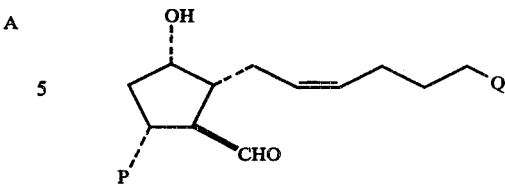

a compound of formula C its optical antipode or a racemic mixture thereof wherein Q is COOR; a compound of formula C its optical antipode or a racemic mixture thereof wherein Q is COOH; a compound of formula C its optical antipode or a racemic mixture thereof wherein Q is COOCH₃; a compound of formula C its optical antipode or a racemic mixture thereof wherein Q is tetrazol-5-yl; a compound of formula C its optical antipode or a racemic mixture thereof wherein Q is CONHSO₂R'''; a compound of formula C its optical antipode or a racemic mixture thereof wherein Q is CONHSO₂CH₃.

an optically active compound of the structure

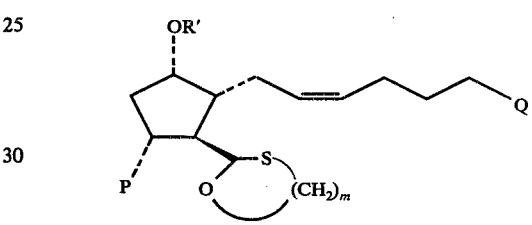

its optical antipode or the racemic mixture thereof wherein R' is selected from the group consisting of hydrogen and

and R" is selected from the group consisting of alkyl of from one to four carbon atoms, β-naphthyl, phenyl, p-biphenyl and phenylalkyl of from seven to nine carbon atoms; Q is selected from the group consisting of tetrazol-5-yl;

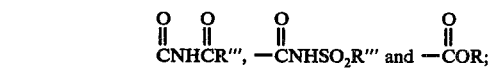

wherein R is selected from the group consisting of hydrogen, alkyl of from one to six carbon atoms, phenyl, phenylalkyl of from seven to nine carbon atoms, β-naphthyl and p-biphenyl; R''' is alkyl of from one to four carbon atoms or phenyl; m is 2 or 3; and P is selected from the group consisting of hydrogen, dimethyl-t-butylsilyloxy, and tetrahydropyran-2-yloxy;

A compound of the structure

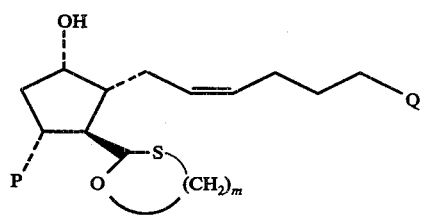

its optical antipode or a racemic mixture thereof, a compound of formula E its optical antipode or a racemic mixture thereof wherein Q is tetrazol-5-yl; a compound of formula E its optical antipode or a racemic mixture thereof wherein Q is COOR; a compound of formula E its optical antipode or a racemic mixture thereof wherein Q is COOH; a compound of formula E its optical antipode or a racemic mixture thereof wherein Q is COOCH₃; a compound of formula E its optical antipode or a racemic mixture thereof wherein Q is CONHSO₂R''''; a compound of formula E its optical antipode or a racemic mixture thereof wherein Q is CONHSO₂CH₃, a compound of the formula:

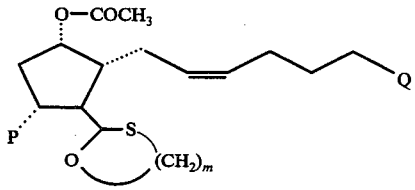

F a compound of formula F its optical antipode or a racemic mixture thereof wherein Q is CONHSO₂R''''; a compound of formula F its optical antipode or a racemic mixture thereof wherein Q is CONHSO₂CH₃; a compound of formula F its optical antipode or a racemic mixture thereof wherein Q is tetrazol-5-yl; a compound of formula F its optical antipode or a racemic mixture thereof wherein Q is COOR; a compound of formula F its optical antipode or a racemic mixture thereof wherein Q is COOH; a compound of formula F its optical antipode or a racemic mixture thereof wherein Q is COOCH₃, and an optically active compound of the structure

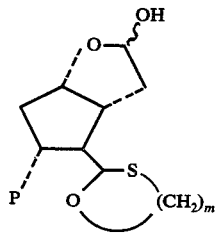

its optical antipode and the racemic mixture thereof wherein

P is selected from the group consisting of hydrogen, tetrahydropyran-2-yloxy and dimethyl-t-butylsilyloxy; and m is two or three.

DETAILED DESCRIPTION OF THE INVENTION

The present invention comprises a process for the preparation of compounds of structure VIII and XIV. Said compounds are useful intermediates in the synthesis of prostaglandins and their analogs as will be described below. Said process illustrated in Scheme B, comprises contacting a compound of structures VII or XIII with the ylide of the appropriate phosphonate of the structure

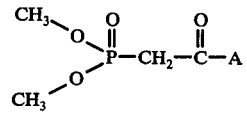

wherein A is as defined above, in a reaction inert solvent at a temperature of from about 0° to 80° C. until reaction is substantially complete.

The reaction is most conveniently conducted by first preparing the ylide under nitrogen in a suitable solvent such as dimethoxyethane, ether or tetrahydrofuran by adding a suitable base such as sodium hydride or n-butyllithium slowly to a solution of the appropriate phosphonate in the same solvent at a reaction temperature of from about 0°–25° C, usually 0°. The formation of the ylide is usually complete within an hour. At this time aldehyde VII or XIII is added, dissolved in the same solvent, and the reaction mixture is stirred at a temperature of from about 0° to 80° C typically at room temperature until reaction is substantially complete, typically for an hour. Aldehyde VII is used to prepare intermediates for the synthesis of prostaglandins and their analogs of the F series and aldehyde XIII is used to prepare intermediates for prostaglandins and their analogs of the E series. The reaction mixture is then brought to pH 6–7 and the product isolated therefrom. Purification of the product is achieved typically by chromatography on silica gel.

Scheme A

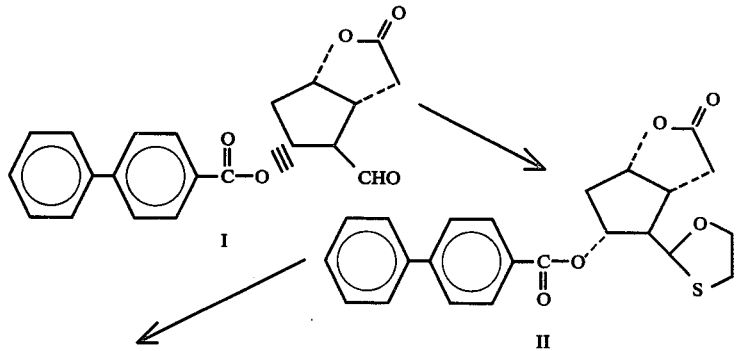

-continued
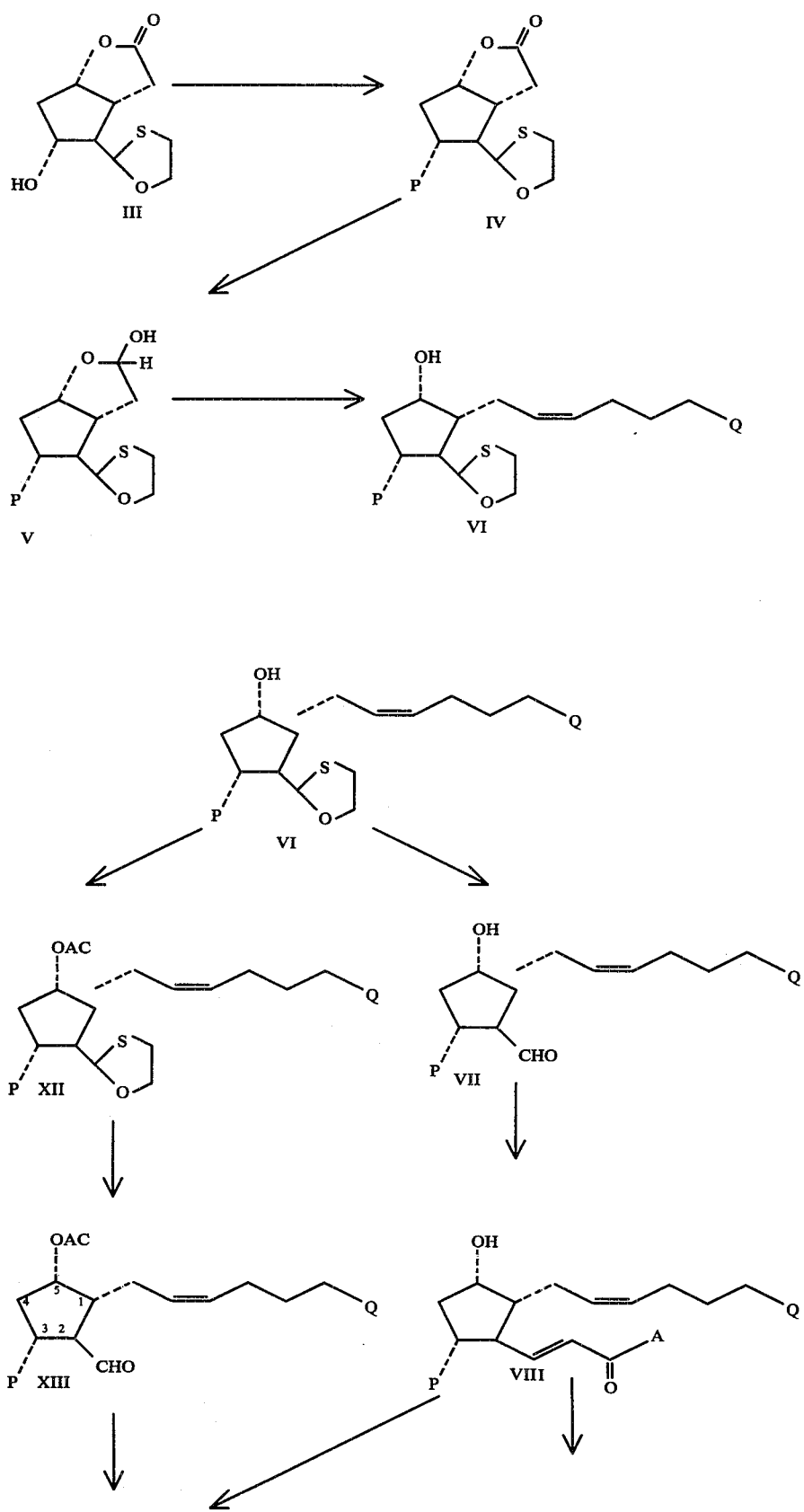

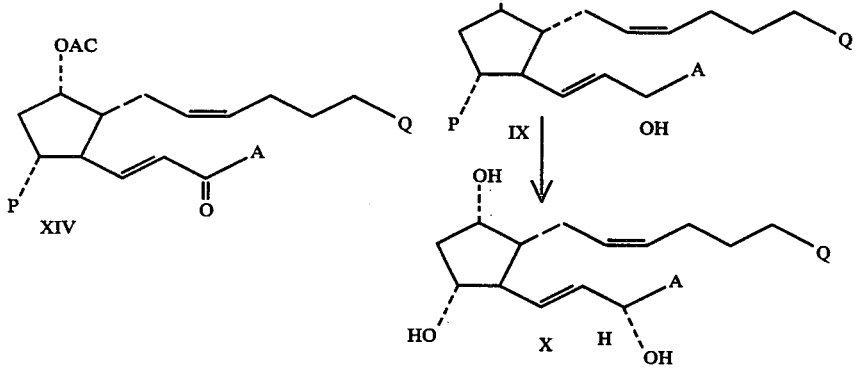

Scheme B

The choice of the phosphonate from which the ylide is prepared is dictated by the structure of the desired final product. For example, when the final product is desired to have a 5-carbon lower side chain at $C_{15}$, (i.e. A is $C_5H_{11}$) the phosphonate used is dimethyl(2-oxoheptyl)-phosphonate, and if the methylenephenoxy lower side chain is desired at $C_{15}$, (i.e. A is $\phi$-$OCH_2$) the phosphonate used is dimethyl 2-oxo-3-phenoxypropyl phosphonate.

According to the present invention the starting materials for the above reaction, i.e. the compounds of structure VII and XIII are prepared from compounds of the structure VI or XII respectively, as shown in Scheme B, removal of the hemithioacetal protecting group. This is accomplished by contacting a solution of said hemithioacetal in a suitable solvent system, typically acetonitrile:water (4:1) with sequentially, an anhydrous alkaline metal carbonate and mercuric chloride. This mixture is stirred until reaction is substantially complete at a reaction temperature of from about 25° to 80° C. Reaction times will vary somewhat with the substrate but typical reaction times are between .5 and 2 hours. Although the reaction may be run in the absence of the alkaline metal carbonate, the most favorable yields are obtained when this material is incorporated in the reaction mixture typically in a molar ratio of about 6:1 ($CaCO_3$:VI or $CaCO_3$:XII). The alkaline metal carbonate most frequently used is calcium carbonate.

The hemithioacetal XII is obtained from compound VI by acylation. This is most commonly achieved using the appropriate acid anhydride in the presence of pyridine although other acylation systems such as acid chlorides or ketenes may be used.

The hemithioacetal VI is the key intermediate in the synthetic sequence of the present invention. It is prepared according to the outline shown in Scheme A. Thus, the desired ylide reagent is prepared from the appropriate phosphonium salt dissolved in dimethylsulphoxide by adding to said solution a solution of sodium methylsulphonylmethide in dimethylsulfoxide in a molar ratio of about 2:1 (anion:salt). Lactol V is then added (dissolved in methylsulphoxide) to the ylide solution prepared above, and the reaction mixture stirred until reaction is substantially complete. Reaction times will vary according to the choice of phosphonium salt and typical reaction times are 1 to 16 hours. The reaction mixture is then poured into water and the product isolated by methods familiar to those skilled in the art. This reaction may be conducted at temperatures of from about −30° to 80° C and the reaction temperature most frequently employed is room temperature. The choice of phosphonium salt is dictated by the structure of the desired final product. In those cases where Q is COOH the salt used is 5-triphenylphosphoniopentanoic acid; where Q is to be COOR the product obtained from the above reaction wherein Q is COOH is esterified by for example a diazoalkane or by treatment of the acid with a mixture dicyclohexyl carbodiimide and the appropriate hydroxyl compound. When it is desired to have Q as tetrazol-5-yl the appropriate phosphonium salt is (4-(tetrazol-5-yl)-n-butyl) triphenylphosphonium bromide. When Q is to be N-methane sulfonylaminocarbonyl, 4-methanesulfonylamino carbonyl-n-butyl)-triphenylphosphonium bromide is used. The proper choice of salt will be obvious to those skilled in the arts as will the manner of preparation of said salts.

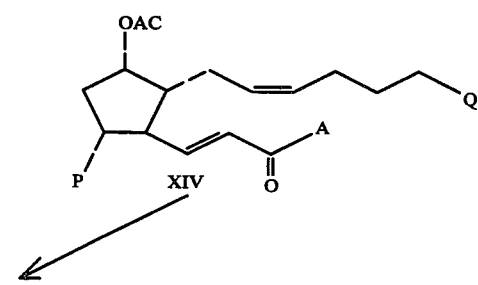

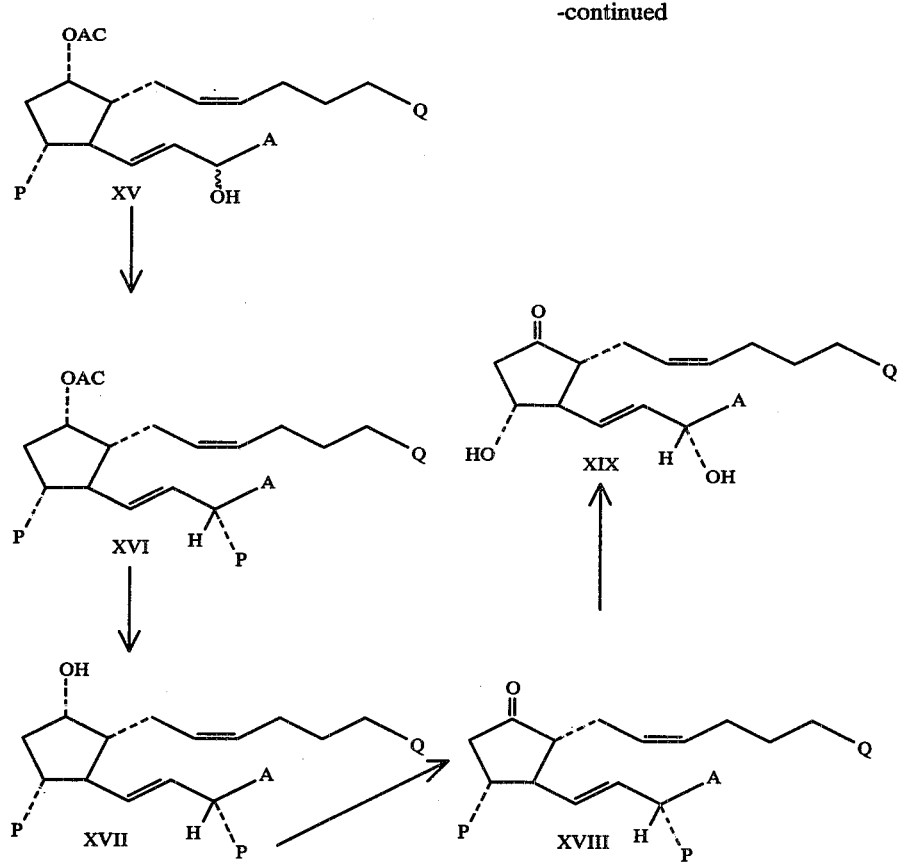

Scheme C

Lactol V is prepared by reduction of lactone IV with diisobutyl aluminum hydride. This reduction is most easily accomplished by contacting lactone IV at low temperatures typically −75° C. in dry toluene with a 20% solution of diisobutyl aluminum hydride in hexane. Higher reaction temperatures may be employed if over reduction does not occur. The diisobutyl aluminum hydride is added to the precooled mixture of lactone IV in toluene over a period of about 20-30 minutes. The reaction mixture is then stirred for an additional 30 minutes and then quenched by the dropwise addition of methanol. The solvents are evaporated under reduced pressure and the product is isolated. The product may be purified by column chromatography on silica gel.

Lactone IV is prepared from lactone III by protection of its hydroxyl group with a suitable acid labile protecting group. Such protecting groups are typically tetrahydropyranyloxy or dimethyl-t-butylsiloxy. Any sufficiently acid-labile group is satisfactory; however, the most usual one is tetrahydropyranyl, which can be incorporated in the molecule by treatment with dihydropyran and an acid catalyst in an anhydrous medium. Lactone III is typically contacted with freshly distilled dihydropyran in dry methylene chloride at a temperature of about 0 to 5° in the presence of an acid catalyst such as para-toluenesulphonic acid. Other non aqueous acid catalysts may likewise be employed. This reaction mixture is stirred until reaction is substantially complete typically one to two hours at a reaction temperature of 0° and the product is then isolated. Lactone III is prepared from parabiphenyl ester II by contacting said parabiphenyl ester with a heterogenous mixture of anhydrous potassium carbonate and absolute methanol.

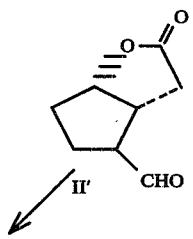

-continued

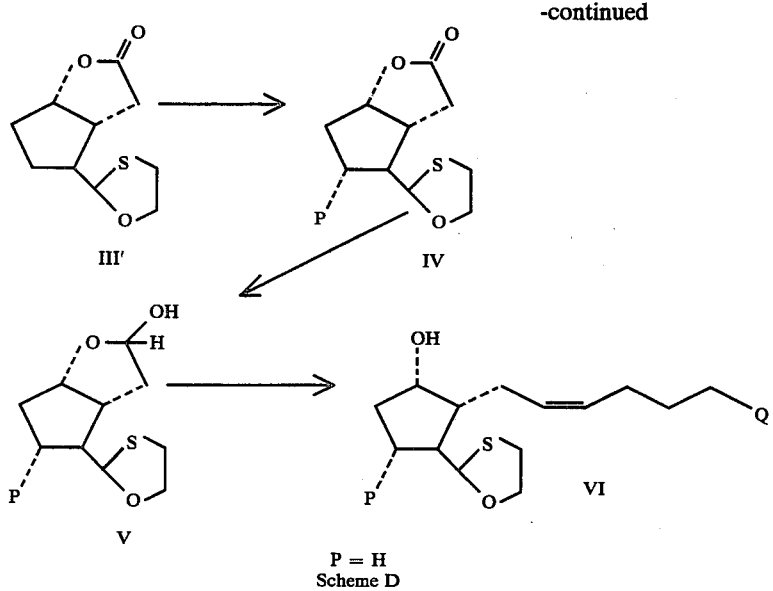

P = H
Scheme D

This reaction is conveniently performed at room temperature for a period of approximately 24 hours. Parabiphenyl ester II is prepared from the known aldehyde I by treatment of said aldehyde with 2-mercaptoethanol in methylene chloride at low temperature, typically 0° under nitrogen in the presence of a Lewis acid catalyst such as boron trifluoride etherate. The reaction time is approximately 10 to 30 minutes. The resulting solution is then warmed to room temperature and stirred for an additional 2 hours. The product is then isolated. Another suitable hemithioacetal protecting group for the aldehyde function may be generated by substituting 3-mercaptopropanol for 2-mercaptoethanol in the above reaction. In this case the protecting group is a six membered hemithioacetal rather than the 5 membered one illustrated in structure II.

For the synthesis of 11-desoxy analogs of prostaglandins the key intermediate VI wherein protecting group P is hydrogen is prepared from the known lactone II' by the same method as that outlined above for the conversion of II into VI (see Scheme D). Lactone II' is known in the art.

As indicated on Scheme B, Intermediate VIII may be converted directly to Intermediate XIV by acylation. As indicated above such acylation reactions are commonly conducted using the acid anhydride of the desired acyl group in the presence of pyridine.

Intermediates XIV and VIII are converted into prostaglandins E and F respectively in the following way:

To produce prostaglandins of the F series Compound VIII is converted into Compound IX by reduction with zinc borohydride. This reduction is usually carried out in dimethoxyethane with a molar ratio of zinc borohydride to Compound VIII of about 1:2. The reaction is usually conducted at room temperature under nitrogen and the reaction times are necessary for complete reduction. Other reducing agents such as lithium trialkyl borohydrides may be employed and solvents such as tetrahydrofuran may be used. The reaction mixture is then cooled in an ice bath, the cold reaction mixture quenched by the addition of sodium bitartrate and the product isolated. The two epimers produced by this reaction are separated by column chromatography on silica gel.

Compound IX is then converted to the desired PGF$_{2\alpha}$ analog by an acidic hydrolysis of the tetrahydropyranyl group. Any acid may be used which does not cause destruction of the molecule in the course of the removal of the protecting group; however, this is accomplished most often by use of 65% aqueous acetic acid, at room temperature for about 18 hours. The product is purified as above.

E series prostaglandins and their analogs may be obtained from Intermediate XIV as shown on Scheme C. The reduction XIV to XV is accomplished in the same manner as the reduction VIII to IX as above. The isomers obtained from this reduction are separated by column chromatography. Alcohol XV is then protected as shown on Scheme A Reaction III to IV under the same conditions as described for that transformation and the resulting protected compound XVI is the hydrolized by contacting it in a suitable solvent or mixture of solvents, such as methanol-tetrahydrofuran (1:1) with one normal aqueous sodium hydroxide solution. This reaction is run at room temperature under nitrogen for periods usually ranging from 8 to 24 hours, although longer reaction times are occasionally necessary to effect complete hydrolysis. The reaction mixture is then acidified by the addition of one normal hydrochloric acid and the acidified solution is extracted with ethylacetate to afford the desired product. This product may be purified, if desired, by column chromatography.

The resulting product XVII is then oxidized to provide Compound XVIII. This reaction is usually achieved using Jones' reagent in acetone at reaction temperatures of from −15 to −20° C. After the appropriate amount of Jones' reagent has been added, the reaction usually stirred for an additional 15 or 20 minutes and then quenched by the addition of isopropyl alcohol. The product is then isolated in the usual way.

Ketone XVIII is then converted to the desired prostaglandin or its analog by the hydrolysis of the protecting groups in the same manner and under the same conditions as described for the transformation of Compound IX to Compound X. The resulting Compound XIX may be then purified, if desired, by column chromatography on silica gel.

Throughout this application all the structural formulas are meant to represent either an optically active compound, its antipode or a racemic mixture of the two.

It will be appreciated by those skilled in the art that the foregoing synthetic sequences of the present invention possess the broad flexibility very much to be desired in the preparation of prostaglandin analogs.

In the sequences described above, a considerable latitude exists in the selection of the protecting group used at a particular stage. Thus, in protecting alcohols, dihydropyranyloxy groups or dimethyl-t-butyl silyl groups may be employed in those situations where the protecting group is represented in the formulae as P. Similarly the acyl group of Compounds XII through XVI may be selected from a broad range of acyl groups such as formyl or alkanoyl of from 2 to 4 carbon atoms, β-naphthyl carbonyl, benzoyl, parabiphenylcarbonyl or phenylalkylcarbonyl wherein an alkyl group may be of from 7 to 9 carbon atoms.

In numerous in vivo and in vitro tests we have demonstrated that the prostaglandin analogs prepared by the process of the present invention possess physiological activities comparable to those exhibited by the natural prostaglandins. These tests include, among others, a test for effect on isolated smooth muscle from guinea pig uterus and rat uterus, inhibition of histamine-induced bronchospasm in the guinea pig, and effect on dog blood pressure, inhibition of stress-induced ulceration in the rat, inhibition of gastric acid and pepsin secretion in rat and dog, inhibition of collagen or ADP-induced blood platelet aggregation and abortifacient activity in rats and guinea pigs by luteolytic and non-luteolytic mechanisms.

The physiological responses observed in these tests are useful in determining the utility of the test substance for the treatment of various natural and pathological conditions. Such determined utilities include: antihypertensive activity, bronchodilator activity, antithromobogenic activity, antiulcer activity, smooth muscle activity [useful as an anti-fertility agent, for the induction of labor, and as an abortifacient], and anti-fertility activity through a mechanism not affecting smooth muscle, for example, luteolytic mechanisms, and the synchronization of the estrous cycle in farm animals.

The novel compounds of this invention possess more selective activity profiles than the corresponding naturally occurring prostaglandins, and in many cases, exhibit a longer duration of action. For example, N-methanesulfonyl 16-phenoxy-ω-tetranorprostaglandin $E_2$ carboxamide which exhibits smooth muscle stimulating activity comparable to $PGE_2$, is inactive in inhibition of histamine-induced bronchospasms in guinea pigs. Furthermore, although the threshold dose of hypotensive response of N-methanesulfonyl 16-phenoxy-ω-tetranor $PGE_2$ carboxamide in dogs is higher than that of $PGE_2$. Another prime example of the therapeutic importance of these prostaglandin analogs is the efficacy of 2-descarboxy-2-(tetrazol-5-yl)-11-desoxy-16-phenyl-ω-tetranorprostaglandin $E_2$ and 2-descarboxy-2-(tetrazol-5-yl)-11-desoxy-16-(p-fluorophenyl)-ω-tetranorprostaglandin $E_2$ which exhibits hypotensive activity of greatly enhanced potency and duration as compared with $PGE_2$ itself. At the same time, the smooth muscle stimulating activity is markedly depressed in comparison with $PGE_2$.

Particularly useful for fertility control, abortion and induction of labor are the 16-phenoxy ω-tetranorprostaglandins 15-indanyl-ω-pentanorprostaglandins and 17-aryl-ω-trisnorprostaglandins of the $E_2$ and $F_{2\alpha}$ series based on especially outstanding smooth muscle stimulating activity, and at the same time reduced diarrheal, bronchodilator or blood pressure effects.

Particularly useful for antiulcer activity are the 16-aryl-ω-tetranorprostaglandins of the $E_2$ series based on outstanding antiulcer and antisecretory activity and at the same time reduced diarrheal and smooth muscle effects.

Also useful for antihypertensive activity are the 2-descarboxy-2-(tetrazol-5-yl)-11-desoxy-16-aryl-ω-tetranorprostaglandins of the $E_2$-series based on outstanding oral hypotensive activity and at the same time reduced diarrheal and smooth muscle effects.

The prostaglandin analogs which have a beta hydroxyl at $C_{15}$ have action which is similar to their epimers. In some cases, however, the selectivity that these compounds display exceeds that of the epimeric compounds.

For induction of abortion, tablets or an aqueous suspension or alcoholic solution of the novel 15-substituted ω-pentanorprostaglandins of the E and F series would appropriately be administered at oral doses of about 0.1–20 mg., with 1–7 doses per day being employed. For intravaginal administration a suitable formulation would be lactose tablets or an impregnated tampon of the same agent. For such treatments suitable doses would be from about 0.1–20 mg/dose with 1–7 doses being employed. For intra-amniotic administration a suitable formulation would be an aqueous solution containing 0.05–10 mg/dose with 1–7 doses being employed. For extra-amniotic administration a suitable formulation would be an aqueous solution containing 0.005–1 mg/dose with 1–5 doses being employed. Alternatively, the 15-substituted-ω-pentanorprostaglandins of the E and F series of this invention can be infused intraveneously for induction of abortion at doses of 0.05–50 μg/minute for a period of from about 1–24 hours.

Another use for the novel 15-substituted-ω-pentanorprostaglandins of the E and F series is as an inducer of labor. For this purpose an ethanol-saline solution is employed as an intravenous infusion in the amount of from about 0.1–10 μg/kg/min for from about 1–24 hours.

Another use for the novel 15-substituted ω-pentanorprostaglandins of the E and F series is for fertility control. For this purpose a tablet is employed for intravaginal or oral administration containing 0.1–20 mg of prostaglandin per dose with 1–7 doses being employed at or following the expected day of menstruation. For synchronization of the estrous cycle in pigs, sheep, cows or horses, a solution or suspension containing 0.03–30 mg/dose of 15-substituted-ω-pentanorprostaglandin of the E and F series is administered subcutaneously from 1–4 days.

15-substituted-ω-pentanorprostaglandins of the E series are useful gastric antisecretory and antiulcer agents. For treatment of peptic ulcers these compounds are administered preferably orally in the form of capsules or tablets at doses of 0.001 to 0.1 mg/kg/day.

The 15-substituted-ω-pentanorprostaglandin analogs of the E series of the present invention are useful hypotensive agents. For treatment of hypertension these drugs could appropriately be administered as an intravenous injection at doses of about 0.5–10 μg/kg or preferably in the form of capsules or tablets at doses of 0.005 to 0.5 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The invention claimed is not limited to the specific conditions cited in the examples to follow. Melting points and boiling points are given in degrees centigrade and are uncorrected. Infrared data is given in microns and NMR data is given in parts per million & using a TMS standard. The following examples are merely illustrative and in no way limit the scope of the appended claims.

EXAMPLE I

2-[3α-(p-biphenylcarboxy)-5α-hydroxy-2β-(2-thioxalanyl)cyclopent-1α-yl]acetic acid, γ-lactone. (II)

To a solution of 2-[3α-(p-biphenylcarboxy)-5α-hydroxy-2β-formyl cyclopent-1α-yl]acetic acid, γ-lactone (21 g, 0.06 mole) in dry methylene chloride (500 ml.) and 2-mercaptoethanol (4.68 g, 0.06 mole) cooled to 0° C under nitrogen was added boron trifluoride etherate (4 ml, 0.03 mole) over a 15 minute period. The resultant solution was warmed to room temperature and stirred for two hours. The reaction was diluted to 900 ml. with more methylene chloride and washed with water (2 × 100 ml.). Drying the methylene chloride layer with anhydrous $Na_2SO_4$ followed by filtering and evaporating under reduced pressure yielded an oil which solidified upon trituration with hexane. Filtration, washing with hexane and drying under vacuum yielded the title compound (23.9 g, 97% yield) m.p. 146°.

Substitution of 3-mercapto-1-propanol for 2-mercaptoethanol in the above procedure will provide the corresponding homologous protected aldehyde which may be converted into the $E_2$- and $F_{2\alpha}$-prostaglandins by the procedures of Examples II–XVIII.

EXAMPLE Ia

2-[5α-hydroxy-2β-(2-thioxalanyl)cyclopent-1α-yl]acetic acid, γ-lactone (II')

To a solution of 2-[5α-hydroxy-2β-formylcyclopent-1α-yl]acetic acid, γ-lactone (18.5 g, 0.12 mole) in dry methylene chloride (500 ml.) and 2-mercaptoethanol (9.36 g, 0.12 mole) cooled to 0° C under nitrogen is added boron trifluoride etherate (8 ml, 0.06 mole) over a 15 minute period. The resultant solution is warmed to room temperature and stirred for two hours. The reaction is diluted to 900 ml. with more methylene chloride and washed with water (2 × 100 ml.). Drying the methylene chloride layer with anhydrous $Na_2SO_4$ followed by filtering and evaporating under reduced pressure yields the title compound.

The product of this Example may be converted into 11-desoxyprostaglandins by the procedures of Examples IV–XVIII. Treatment of the formyllactone starting material with 3-mercapto-1-propanol under the above described conditions provides the corresponding protected aldehyde which may be converted into the 11-desoxyprostaglandins by the procedures of Examples IV–XVIII.

EXAMPLE II

2-[3α,5α-dihydroxy-2β-(2-thioxalanyl)cyclopent-1α-yl]acetic acid, γ-lactone (III)

A heterogeneous mixture of crude 2-[3α-(p-biphenylcarboxy)-5α-hydroxy-2β-(2-thioxalanyl)cyclopent-1]-yl acetic acid, γ-lactone (23.5 g., 0.057 mole) absolute methanol (230 ml.) and finely powdered anhydrous potassium carbonate (3.95 g., 0.028 mole) was stirred at room temperature overnight. The precipitated solid was filtered and washed with methanol. The filtrate was evaporated to approximately 100 ml. and cooled in ice. To the cooled solution was added 0.1N HCl dropwise to bring the solution to a pH of 3, and the precipitated solids were filtered off. The aqueous layer was saturated with solid sodium chloride and extracted with ethyl acetate (3 × 50 ml.). Drying the combined organic layer with anhydrous $Na_2SO_4$ followed by evaporation gave the title compound (12.6 g., 96% yield).

EXAMPLE III

2-[3α-(tetrahydropyran-2-yloxy)-5α-hydroxy-2β-(2-thioxalanyl) cyclopent-1α-yl]acetic acid, γ-lactone (IV)

To a cooled solution (0°–5°) of crude 2-[3α,5α-dihydroxy-2β-(2-thioxalanyl)cyclopent-1α-yl]acetic acid, γ-lactone (2.5 g, 10.9 mmoles) and freshly distilled dihydropyran (1.47 ml, 16.3 mmoles) in dry methylene chloride (25 ml.) was added p-toluenesulfonic acid monohydrate (250 mg, 1.31 mmoles). The reaction mixture was stirred for 1.5 hours at 0° C, then diluted with ether (60 ml.). The organic solution was washed with saturated sodium bicarbonate (10 ml.), saturated brine (10 ml.) and dried over anhydrous sodium sulfate. Concentration under vacuum afforded the title compound (3.4 g, 100% yield) as an oil.

EXAMPLE IIIa

2-[3α-(dimethyl-t-butylsilyloxy)-5α-hydroxy-2β-(2-thioxalanyl)cyclopent-1α-yl]acetic acid, γ-lactone (IV)

A mixture of 2-[3α,5α-dihydroxy-2β-(2-thioxalanyl)-cyclopent-1α-yl]acetic acid, γ-lactone (2.25 g, 10 mmoles), dimethyl-t-butylsilyl chloride (1.88 g, 12.5 mmoles) and imidazole (1.87 g, 27.5 mmoles) in 5 ml of dimethylformamide is stirred under nitrogen at 37° for 18 hours. The reaction is concentrated under reduced pressure and diluted with methylene chloride. The organic solution is washed with water, dried (anhydrous magnesium sulfate) and concentrated under reduced pressure. Purification of the crude product by silica gel chromatography provides the title compound.

The product of this Example may be converted into the 11-hydroxyprostaglandins by the procedures of Examples IV–XVII.

EXAMPLE IV

2-[3α-(tetrahydropyran-2-yloxy)-5α-hydroxy-2β-(2-thioxalanyl)cyclopent-1α-yl]acetaldehyde, γ-hemiacetal (V)

To a solution, cooled to −75° under nitrogen, of crude 2-[3α-(tetrahydropyran-2-yloxy)-5α-hydroxy-2β-(2-thioxalanyl)cyclopent-1α-yl]acetic acid, γ-lactone (3.24 g, 10.3 m moles) in dry toluene (50 ml.) was added over a period of 25 minutes a 20% solution of diisobutylaluminum hydride in hexane (14.9 ml, 12.0 m moles). After an additional 30 minutes the reaction was quenched by dropwise addition of methanol and allowed to warm to room temperature. The toluene was evaporated under reduced pressure and the residue diluted with ether (200 ml.). The organic solution was washed with a 50% sodium potassium tartrate solution (3X), saturated brine, then dried with anhydrous $Na_2SO_4$ and was concentrated to afford the title compound (3.1 g, 95% yield) as an oil. The product was purified by column chromatography on 90 g of Baker silica gel (60-200 mesh) using benzene→ ethyl acetate as eluents to give the pure title compound (2.9 g).

The product of this Example may be treated with a phosphorane of the structure

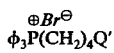

wherein Q' is selected from the group consisting of tetrazol-5-yl,

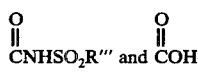

wherein R''' is alkyl of from one to four carbon atoms according to the procedures of Example V. The product of this reaction may be converted into the $E_2$- and $F_{2\alpha}$-prostaglandins by the procedures of Examples VII--IX and XI-XVIII.

EXAMPLE V

7-[2β-(2-thioxalanyl)-3α-(tetrahydropyran-2-yloxy)-5α-hydroxycyclopent-1α-yl]-cis-5-heptenoic acid (VI)

To a solution of 5-triphenylphosphoniopentanoic acid (23.04 5 g, 52.0 mmoles) in dry dimethyl sulfoxide (46 ml.) was added dropwise an approximately 2.0N solution of sodium methylsulfinylmethide (49.3 ml, 98.6 mmoles) in dimethyl sulfoxide. To the resultant red solution was added over the course of 1.0 hour a solution of 2-[2β-(2-thioxalanyl)-3α-(tetrahydropyran-2-yloxy)-5α-hydroxycyclopent-1α-yl]-acetaldehyde, γ-hemiacetal (6.6 g, 20.8 mmoles) in dry dimethyl sulfoxide (63 ml.). After being stirred for an additional half hour, the reaction was poured into ice-water (600 ml.). The basic aqueous solution was extracted with 2:1 mixture of ethyl acetate:ether (2 × 300 ml.). The cold aqueous layer was covered with ethyl acetate and acidified to pH∼3 with 10% hydrochloric acid. The aqueous layer was further extracted with ethyl acetate (2 × 200 ml) and the combined organic extracts were washed with water followed by brine. Drying the organic layer over anhydrous sodium sulfate and concentrating afforded a yellow oil weighing 20 g. Addition of 150 ml. of a mixture of ethyl acetate:ether (2:1) precipitated a solid which was filtered, washed with ether and the filtrate evaporated. The yield of crude title compound was 10.2 g. (120%) which was used directly in the next step.

The product of this Example may be esterified according to the procedure of Example Va with an alkyl diazo compound of from one to six carbon atoms or phenylalkyl diazo compound of from seven to nine carbon atoms. Alternatively, one equivalent of the product of this Example may be contacted with ten equivalents of phenol, β-naphthol or p-phenylphenol and 1.2 equivalents of dicyclohexylcarbodiimide. The resultant esters may be converted into the $E_2$- and $F_{2\alpha}$- prostaglandins by the procedures of Examples VI-IX and XI-XVII.

EXAMPLE Va

Methyl 7-[2β-(2-thioxalanyl)-3α-(tetrahydropyran-2-yloxy)-5α-hydroxycyclopent-1α-yl]-cis-5-heptenoate (VI)

A solution of 7-[2β-(2-thioxalanyl)-3α-(tetrahydropyran-2-yloxy)-5α-hydroxycyclopent-1α-yl]-cis-5-heptenoic acid (520 mg, 1.3 mmoles) in 5 ml of anhydrous ether is titrated at room temperature with an ethereal diazomethane solution until the yellow color persists for 5 minutes. The reaction is then decolorized by the dropwise addition of glacial acetic acid. The ethereal solution is then washed with saturated sodium bicarbonate and saturated brine, is dried (anhydrous magnesium sulfate), and is concentrated under reduced pressure to provide the title compound.

The product of this Example may be converted into $E_2$- and $F_{2\alpha}$-prostaglandins by the procedures of Examples VI-IX and XI-XVII.

EXAMPLE VI

7-[2β-formyl-3α-(tetrahydropyran-2-yloxy)-5α-hydroxycyclopent-1α-yl]-cis-5-heptenoic acid (VII)

To a solution of 7-[2β-(2-thioxalanyl)-3α-(tetrahydropyran-2-yloxy)-5α-hydroxycyclopent-1α-yl]-cis-5-heptenoic acid (2.0 g, 0.005 mole) 4:1 acetonitrile:water (85 ml.) was added sequentially anhydrous calcium carbonate (2.87 g, 0.029 mole) and mercuric chloride (5.4 g, 0.020 mole). The mixture was stirred and heated at 50° C. under nitrogen for a half hour. The mixture was filtered through celite and washed with ether (250 ml.). The combined filtrate was stirred and treated with 1N hydrochloric acid (3 ml.). The ether layer was separated and washed with brine (3 × 15 ml.). Drying over anhydrous sodium sulfate and concentration at reduced pressure afforded 1.7 g (100%) of the title compound as an oil.

The product of this Example may be treated with a phosphonate of the structure

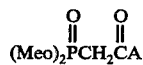

wherein A is selected from the group consisting of alkyl of from four to eight carbon atoms, 2-indanyl, and a substituent of the structure $Ar(CH_2)_n-$ and $Ar'OCH_2-$ wherein n is an integer of from one to two and Ar is selected from the group consisting of α-naphthyl, β-naphthyl, 60 -furyl, α-thienyl, phenyl and monosubstituted phenyl and the substituent of said monosubstituted phenyl is selected from the group consisting of fluoro, chloro, trifluoromethyl, phenyl and alkyl and alkoxy of from one to six carbon atoms; and Ar' is selected from the group consisting of phenyl and monosubstituted phenyl; and the substituent on said monosubstituted phenyl is selected from the group consisting of fluoro, chloro, trifluoromethyl, phenyl and alkyl and alkoxy of from one to six carbon atoms according to the procedures of Examples VII or XIII. The product of this reaction may be converted into the $PGF_{2\alpha'}$s by the procedures of Example VIII and IX.

EXAMPLE VII

9α-hydroxy-11α-(tetrahydropyran-2-yloxy)-15-oxo-cis-5-trans-13-prostadienoic acid (VIII)

To a solution, under nitrogen, of dimethyl(2-oxo-heptyl)phosphonate (2 g, 0.009 mole) in dimethoxyethane (30 ml.) cooled to 0° C was added dropwise 2.2 M n-butyl lithium (3.96 ml, 0.0087 mole). After stirring for one hour 7-[2β-formyl-3α-(tetrahydropyran-2-yloxy)-5α-hydroxycyclopent-1α-yl]-cis-5-heptenoic acid (1.02 g, 0.003 mole) dissolved in dimethoxyethane (6 ml.) was added quickly and the mixture stirred at room temperature for a half hour, it was brought to pH~7 with glacial acetic acid. The neutralized solution was concentrated by rotary evaporation and the resultant solid was slurried in benzene and filtered. Concentration of the filtrate afforded the crude title compound which was purified by chromatography on silica gel using benzene→ethylacetate as eluant to give the pure title compound (710 mg).

The product of this Example may be acylated according to the procedure of Example XI to form the product of Example XIII.

EXAMPLE VIII

9α-15ξ-dihydroxy-11α-(tetrahydropyran-2-yloxy)-cis-5-trans-13-prostadienoic acid (IX)

To a solution of 9α-hydroxy-11α-(tetrahydropyran-2-yloxy)-15-oxo-cis-5-trans-13-prostadienoic acid (0.15 g, 0.343 m mole) in dimethoxyethane (3 ml.) was added a 0.5 M solution of zinc borohydride (1.75 ml., 0.17 m mole) in dimethoxyethane. The reaction was stirred at room temperature under nitrogen for 2.5 hours then was cooled in ice. The cold reaction mixture was quenched by the addition of a saturated sodium bitartrate solution dropwise until hydrogen evolution ceased. The mixture was diluted with ethyl acetate (25 ml.), acidified to about pH 4 with cold 1N HCl with rapid stirring. The ethyl acetate layer was dried with sodium sulfate and concentrated to afford the oily epimeric mixture of the title compounds weighing 0.13 g, ($R_f$ 0.25 on t.l.c. using 15:5:2 mixture of benzene:dioxan:-formic acid as eluant), suitable for directly using in the next step.

EXAMPLE IX

PGF$_{2α}$ (X)

A homogeneous solution of crude 9α,15-dihydroxy-11α-(tetrahydropyran-2-yloxy)-cis-5-trans-13-prostadienoic acid (0.117 g, 0.267 mmole) in a 65:35 mixture of glacial acetic acid:water (5 ml.) was stirred under nitrogen at room temperature for 16 hours then was concentrated by rotary evaporation followed by oil pump at 25° C. The resultant oil was chromatographed on 5 g silica gel (CC-7) using chloroform→ethyl acetate to give 15 mg 15-epi PGF$_{2α}$ followed by 30 mg of PGF$_{2α}$, identical with an authentic sample by IR and NMR.

EXAMPLE X

N-Methanesulfonyl 7-[2β-(1,3-oxathialan-2-yl)-3α-(tetrahydropyran-2-yloxy)-5α-hydroxycyclopent-1α-yl]-cis-5-heptenamide (VI)

To a solution of 27.0 g. (52.0 mmoles) of (4-methanesulfonylaminocarbonyl-n-butyl)triphenylphosphonium bromide in 46 ml. of dimethyl sulfoxide is added dropwise 49.3 ml. (98.6 mmoles) of a 2.0M solution of sodium methylsulfonylmethide in dimethyl sulfoxide. To the resultant red solution is added over the course of 15 minutes a solution of 6.6 g. (20.8 mmoles) of the hemiacetal prepared in Example IV in 63 ml. of dimethyl sulfoxide. After being stirred for an additional 2.0 hours, the reaction is poured onto 600 ml. of ice-water. The cold aqueous layer is covered with ethyl acetate and acidified to pH~3 with 10% hydrochloric acid. The acidified aqueous layer is further extracted with ethyl acetate (2 × 200 ml.) and the combined organic extracts are washed with water followed by brine. Drying the organic layer over anhydrous sodium sulfate and concentration affords the crude product which is triturated with ether. Concentration of the ether provides N-methanesulfonyl 7-[2β-(1,3-oxathialan-2-yl)-3α-(tetrahydropyran-2-yloxy)-5α-hydroxycyclopent-1α-yl)]-cis-5-heptenamide (VI).

The product of this Example may be acylated according to the procedure of Example XI employing either

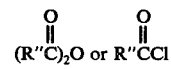

wherein R″ is alkyl of from one to four carbon atoms, β-naphthyl, phenyl, p-biphenyl and phenylalkyl of from seven to nine carbons. This product may be converted into the E$_2$-prostaglandins according to the procedures of Examples XII–XVIII.

EXAMPLE XI

N-Methanesulfonyl 7-[2β-(1,3-oxathialan-2-yl)-3α-(tetrahydropyran-2-yloxy)-5α-acetoxycyclopent-1α-yl]-cis-5-heptenamide (XII).

A mixture of 1.69 g. (3.54 mmoles) of the crude hydroxy compound VI prepared in Example X, 5.0 ml. of pyridine and 0.368 ml. (3.89 mmoles) of acetic anhydride is stirred under nitrogen at 50° overnight. The mixture is then cooled to room temperature and is diluted with ether (75 ml.). The ethereal solution is washed with water (1x) and with saturated copper sulfate (3x), is dried (anhydrous magnesium sulfate), and is concentrated to afford the desired N-methanesulfonyl 7-[2β-(1,3-oxathialan-2-yl)-3α-(tetrahydropyran-2-yloxy)-5α-acetoxycyclopent-1α-yl]-cis-5-heptenamide. (XII)

EXAMPLE XII

N-Methanesulfonyl 7-[2β-formyl-3α-(tetrahydropyran-2-yloxy)-5α-acetoxycyclopent-1α-yl]-cis-5-heptenamide (XIII).

To a solution of 2.9 g. (5.0 mmoles) of the hemithioacetal XII prepared in Example XI in 85 ml. of acetonitrile:water (4:1) is added sequentially 2.87 g. (0.029 mmole) anhydrous calcium carbonate and 5.4 g. (0.020 mmole) mercuric chloride. The mixture is stirred and heated at 50° under nitrogen for 0.5 hr. The mixture is filtered through celite and washed with 250 ml. ether. The combined filtrate is stirred and treated with 3 ml. of 1N hydrochloric acid. The ether layer is separated and washed with brine (3 × 15 ml.). Drying over anhydrous sodium sulfate and concentration at reduced pressure afforded the desired N-methanesulfonyl 7-[2β-formyl-3α-(tetrahydropyran-2-yloxy)-5α-acetoxycyclopent-1α-yl]-cis-5-heptenamide. (XIII)

The product of this Example may be treated with a phosphonate of the structure

wherein A is selected from the group consisting of alkyl of from four to eight carbon atoms, 2-indanyl, and a substituent of the structure Ar(CH$_2$)$_n$— and Ar'OCH$_2$— wherein n is an integer of from one to two and Ar is selected from the group consisting of α-naphthyl, β-naphthyl, α-furyl, α-thienyl, phenyl and monosubstituted phenyl and the substituent of said monosubstituted phenyl is selected from the group consisting of fluoro, chloro, trifluoromethyl, phenyl and alkyl and alkoxy of from one to six carbon atoms; and Ar' is selected from the group consisting of phenyl and monosubstituted phenyl; and the substituent on said monosubstituted phenyl is selected from the group consisting of fluoro, chloro, trifluoromethyl, phenyl and alkyl and alkoxy of from one to six carbon atoms according to the procedures of Examples VII or XIII. The product of this reaction may be converted into the E$_2$-prostaglandins by the procedures of Examples XIV–XVIII.

EXAMPLE XIII

N-Methanesulfonyl 9α-acetoxy-11α-(tetrahydropyran-2-yloxy)-15-oxo-5-cis-13-trans-16-phenoxy-ω-tetranorprostadienamide (XIV).

To a suspension of 220 mg. (5.22 mmoles) of a 57.0% dispersion of sodium hydride in mineral oil in 20 ml. of tetrahydrofuran is added 1.34 g. (5.22 mmoles) of dimethyl 2-oxo-3-phenoxypropyl phosphonate. The mixture is stirred at room temperature for 1 hour under nitrogen, then a solution of 1.23 g. (2.37 mmoles) of the crude aldehyde XIII prepared in Example XII in 4 ml. of tetrahydrofuren is added. The resultant mixture is stirred at room temperature for 2.0 hours under nitrogen. The reaction is then quenched by the addition of glacial acid to pH∼6 and is concentrated by rotary evaporation.

The resultant mixture is dissolved in ethyl acetate, the organic layer is washed with 0.1N hydrochloric acid, water and saturated brine, is dried (anhydrous magnesium sulfate) and concentrated. Purification of the crude product by column chromatography affords the desired N-methanesulfonyl 9α-acetoxy-11α-(tetrahydropyran-2-yloxy)-15-oxo-5-cis-13-trans-16-phenoxy-ω-tetranorprostadienamide. (XIV)

EXAMPLE XIV

N-Methanesulfonyl 9α-acetoxy-11α-(tetrahydropyran-2-yloxy)-15α-hydroxy-16-phenoxy-5-cis-13-trans-ω-tetranorprostadienamide (XVa) and N-Methanesulfonyl 9α-acetoxy-11α-(tetrahydropyran-2-yloxy)-15β-hydroxy-16-phenoxy-5-cis-13-trans-ω-tetranorprostadienamide. (XVb).

To a solution, cooled to −78° under nitrogen, of 1.24 g. (2.1 mmoles) of the lactone XIV prepared in Example XIII in 12 ml. of tetrahydrofuran is added 4.3 ml of a 1.0M solution of lithium triethylborohydride in tetrahydrofuran. The mixture is stirred in the cold for 45 minutes then quenched by the addition of a 9:1 mixture of water:acetic acid. The mixture is let warm then diluted with ethyl acetate. The organic solution is washed with water (2 ×) and saturated brine, is dried (anhydrous magnesium sulfate) and concentrated. Purification of the crude product by column chromatography provides first N-methanesulfonyl 9α-acetoxy-11α-(tetrahydropyran-2-yloxy)-15β-hydroxy-16-phenoxy-5-cis-13-trans-ω-tetranorprostadienamide (XVb) and further elution provides N-methanesulfonyl 9α-acetoxy-11α-(tetrahydropyran-2-yloxy)-15α-hydroxy-16-phenoxy-5-cis-13-trans-ω-tetranorprostadienamide. (XVa)

The 15β-compounds of this Example may be converted into the 15-epi-E-prostaglandins by the procedures of Examples XV–XVIII.

EXAMPLE XV

N-Methanesulfonyl 9α-acetoxy-11α,15α-bis-(tetrahydropyran-2-yloxy)-16-phenoxy-5-cis-13-trans-ω-tetranorprostadienamide. (XVI)

A mixture of 0.303 g. (0.510 mmole) of the chromatographed alcohol XVa of Example XIV, 0.14 ml. (1.53 mmoles) of dihydropyran, 4.2 ml. of methylene chloride, and 1 crystal of p-toluenesulfonic acid monohydrate is stirred at room temperature under nitrogen for 20 minutes. The reaction mixture is then diluted with ether, is washed with water and saturated brine, is dried (anhydrous magnesium sulfate), and concentrated to give the desired N-Methanesulfonyl 9α-acetoxy-11α,-15α-bis-(tetrahydropyran-2-yloxy)-16-phenoxy-5-cis-13-trans-ω-tetranorprostadienamide. (XVI)

EXAMPLE XVI

N-Methanesulfonyl 9α-hydroxy-11α,15α-bis-(tetrahydropyran-2-yloxy)-16-phenoxy-5-cis-13-trans-ω-tetranorprostadienamide. (XVII)

A homogenous solution of 0.295 g. (0.436 mmole) of the crude bis-THP ester XVI prepared in Example XV, 1.3 ml. (1.30 mmoles) of a 1.0N aqueous sodium hydroxide solution, 1.3 ml. of methanol, and 1.3 ml. of tetrahydrofuran is stirred under nitrogen overnight. The reaction is then quenched by the addition of 1.30 ml. (1.30 mmoles) of a 1.0N aqueous hydrochloric acid solution. The quenched solution is diluted with ethyl acetate. The organic layer is dried (anhydrous magnesium sulfate) and concentrated. The crude product is purified by column chromatography to afford the desired N-methanesulfonyl 9α-hydroxy-11α,15α-bis-(tetrahydropyran-2-yloxy)-16-phenoxy-5-cis-13-trans-ω-tetranorprostadienamide. (XVII)

EXAMPLE XVII

N-Methanesulfonyl 9-oxo-11α,15α-bis-(tetrahydropyran-2-yloxy)-16-phenoxy-5-cis-13-trans-ω-tetranorprostadienamide. (XVIII)

To a solution, cooled under nitrogen to −15° to −20° of 236 mg. (0.371 mmole) of the chromatographed methanesulfonimide XVII in Example XVI in 4.0 ml. of acetone is added dropwise 0.163 ml. (0.408 mmole) of Jones' reagent. The reaction is stirred in the cold for 15 minutes then is quenched by the addition of 0.194 ml. of isopropanol. The quenched reaction is stirred in the cold for 5 minutes then is diluted with ethyl acetate. The organic solution is washed with water (2x) and saturated brine (1x), is dried (anhydrous magnesium sulfate), and is concentrated to afford the desired N-methanesulfonyl 9-oxo-11α,15α-bis-(tetrahydropyran-2-yloxy)-16-phenoxy-5-cis-13-trans-ω-tetranorprostadienamide. (XVIII)

EXAMPLE XVIII

N-Methanesulfonyl 9-oxo-11α,15α-dihydroxy-16-phenoxy-5-cis-13-trans-ω-tetranorprostadienamide. (XIX)

A homogenous solution of 208 mg. (0.328 mmole) of the crude THP ether XVIII of Example XVII in 5 ml. of a 65:35 mixture of acetic acid:water is stirred under nitrogen at ambient temperature for 18 hours. The reaction is concentrated by rotary evaporation followed by oil pump. The crude, product is purified by column chromatography on silica gel to provide the desired N-methanesulfonyl 9-oxo-11α,15α-dihydroxy-16-phenoxy-5-cis-13-trans-ω-tetranorprostadienamide. (XIX)

What is claimed is:

1. An optically active compound of the structure

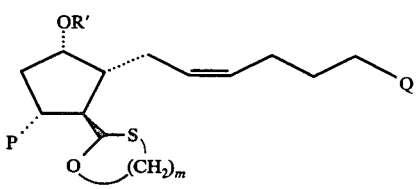

its optical antipode or the racemic mixture thereof wherein R' is selected from the group consisting of hydrogen and

CR'' and R'' is selected from the group consisting of alkyl of from one to four carbon atoms, β-naphthyl, phenyl, p-biphenyl and phenylalkyl of from seven to nine carbon atoms; Q is selected from the group consisting of tetrazol-5-yl;

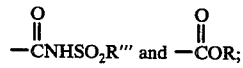
—CNHSO$_2$R''' and —COR;

wherein R is selected from the group consisting of hydrogen, alkyl of from one to six carbon atoms, phenyl, phenylalkyl of from seven to nine carbon atoms, β-naphthyl and p-biphenyl; R''' is alkyl of from one to four carbon atoms; m is 2 or 3; and P is selected from the group consisting of hydrogen, dimethyl-t-butylsilyloxy, and tetrahydropyran-2-yloxy.

2. A compound of claim 1 of the structure

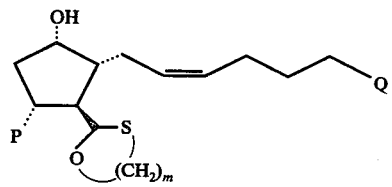

3. A compound of claim 2 wherein Q is tetrazol-5-yl.
4. A compound of claim 2 wherein Q is

—COR.

5. A compound of claim 2 wherein Q is

CNHSO$_2$R'''.

6. A compound of claim 1 of the structure.

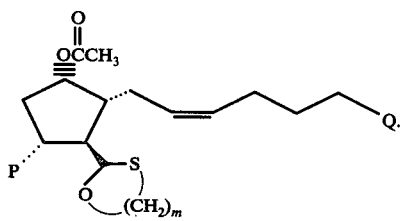

7. A compound of claim 6 wherein Q is tetrazol-5-yl.
8. A compound of claim 6 wherein Q is

—COR.

9. A compound of claim 6 wherein Q is

—CNHSO$_2$R'''.

10. The compound of claim 9 wherein R''' is methyl, P is tetrahydropyran-2-yloxy and m is 2.

* * * * *